United States Patent [19]

Chakrabarti et al.

[11] Patent Number: 4,959,208
[45] Date of Patent: * Sep. 25, 1990

[54] ACTIVE AGENT DELIVERY DEVICE

[75] Inventors: Paritosh M. Chakrabarti, Pittsburgh, Pa.; John M. Denison, Westmount, Canada; Harlan B. Johnson, Rittman; Malcolm Korach, Akron, both of Ohio; Dennis D. Leatherman, Pittsburgh, Pa.; Linda P. Reinhardt, Lake Charles, La.; Richard A. Schwarz, Akron; Robert B. Simmons, Norton, both of Ohio

[73] Assignee: PPG Industries, Inc., Pittsburgh, Pa.

[*] Notice: The portion of the term of this patent subsequent to May 23, 2006 has been disclaimed.

[21] Appl. No.: 264,242

[22] Filed: Oct. 28, 1988

Related U.S. Application Data

[63] Continuation-in-part of Ser. No. 250,015, Sep. 27, 1988, which is a continuation-in-part of Ser. No. 110,147, Oct. 19, 1987, abandoned.

[51] Int. Cl.$^5$ .................. A61K 31/74; A61K 31/765; A61K 9/50; A61K 9/14
[52] U.S. Cl. ......................................... 424/78; 424/83; 424/486; 424/484; 424/487; 521/61; 521/62; 521/64; 514/263
[58] Field of Search ............... 424/78, 83, 486, 484, 424/487; 521/61, 62, 64; 514/963

[56] References Cited

U.S. PATENT DOCUMENTS

| | | | |
|---|---|---|---|
| 2,823,421 | 2/1958 | Scarlett | 18/57 |
| 2,940,830 | 6/1960 | Thornhill | 23/182 |
| 3,351,495 | 11/1967 | Larsen et al. | 136/146 |
| 3,426,754 | 2/1969 | Bierenbaum et al. | 128/156 |
| 3,598,122 | 8/1971 | Zaffaroni | 128/268 |
| 3,598,123 | 8/1971 | Zaffaroni | 128/268 |
| 3,742,951 | 7/1973 | Zaffaroni | 128/268 |
| 3,844,865 | 10/1974 | Elton et al. | 156/229 |
| 3,920,785 | 11/1975 | Druin et al. | 264/210 R |
| 3,921,636 | 11/1975 | Zaffaroni | 128/260 |
| 3,926,188 | 12/1975 | Baker et al. | 128/260 |
| 3,970,593 | 3/1975 | Elton et al. | 161/159 |
| 4,053,580 | 10/1977 | Chien et al. | 424/15 |
| 4,169,014 | 9/1979 | Goldberg | 435/182 |
| 4,194,041 | 3/1980 | Gore et al. | 428/315 |
| 4,230,105 | 10/1980 | Harwood | 128/156 |
| 4,237,083 | 12/1980 | Young et al. | 264/41 |
| 4,289,749 | 9/1981 | Keith et al. | 424/28 |
| 4,292,301 | 9/1981 | Keith et al. | 424/28 |
| 4,292,302 | 9/1981 | Keith et al. | 424/28 |
| 4,292,303 | 9/1981 | Keith et al. | 424/28 |
| 4,293,565 | 10/1981 | Cordes et al. | 424/285 |
| 4,294,820 | 10/1981 | Keith et al. | 424/28 |
| 4,362,737 | 12/1982 | Schafer et al. | 424/273 R |
| 4,411,893 | 10/1983 | Johnson et al. | 424/181 |
| 4,443,511 | 4/1984 | Worden et al. | 428/198 |
| 4,501,793 | 2/1985 | Sarada | 428/315.5 |
| 4,525,340 | 6/1985 | Lange et al. | 424/16 |
| 4,539,256 | 9/1985 | Shipman | 428/315.5 |
| 4,613,544 | 9/1986 | Burleigh | 428/315.5 |
| 4,648,417 | 3/1987 | Johnson et al. | 134/105 |
| 4,681,750 | 7/1987 | Johnson et al. | 423/339 |
| 4,734,229 | 3/1988 | Johnson et al. | 264/40.6 |
| 4,756,844 | 7/1988 | Walles et al. | 252/95 |
| 4,791,144 | 12/1988 | Nagou | 521/90 |
| 4,833,172 | 5/1989 | Schwarz et al. | 521/62 |

FOREIGN PATENT DOCUMENTS

0191615 8/1986 European Pat. Off.
62-227932 10/1987 Japan.

OTHER PUBLICATIONS

H. J. Sanders, *Chemical & Engineering News*, Apr. 1, 1985, pp. 31-40, 44-45, 47-48.
*Membrane & Separation Technology News*, Dec. 1987, pp. 1-2.

*Primary Examiner*—Joseph L. Schofer
*Assistant Examiner*—Carmen B. Pili-Cuptic
*Attorney, Agent, or Firm*—George D. Morris

[57] ABSTRACT

An active agent delivery device comprises (a) microporous material comprising a matrix consisting essentially of linear ultrahigh molecular weight polyolefin, a large proportion of finely divided water-insoluble filler of which at least about 50 percent by weight is siliceous, and interconnecting pores; and (b) a releasable active agent or precursor thereof associated with at least a portion of the filler.

14 Claims, No Drawings

ACTIVE AGENT DELIVERY DEVICE

This application is a continuation-in-part of application Ser. No. 250,015, filed Sept. 27, 1988, which is a continuation-in-part of application Ser. No. 110,147, filed Oct. 10, 1987 now abandoned.

The present invention is directed to an active agent delivery device based on microporous material characterized by a matrix consisting essentially of linear ultrahigh molecular weight polyolefin, a very large proportion of finely-divided particulate siliceous filler, and a high void content.

Accordingly, one embodiment of the invention is an active agent delivery device which releases active agent over a prolonged period of time comprising (a) microporous material comprising (1) a matrix consisting essentially of essentially linear ultrahigh molecular weight polyolefin which is essentially linear ultrahigh molecular weight polyethylene having an intrinsic viscosity of at least about 18 deciliters/gram, essentially linear ultrahigh molecular weight polypropylene having an intrinsic viscosity of at least about 6 deciliters/gram, or a mixture thereof, (2) finely divided particulate substantially water-insoluble filler, of which at least about 50 percent by weight is siliceous, distributed throughout the matrix, the filler constituting from about 50 percent to about 90 percent by weight of the microporous material, and (3) a network of interconnecting pores communicating throughout the microporous material, the pores constituting at least about 35 percent by volume of the microporous material, and (b) a releasable active agent or precursor thereof associated with at least a portion of the filler.

Another embodiment of the invention is a process for producing an active agent delivery device which releases active agent over a prolonged period of time comprising treating microporous material comprising (a) a matrix consisting essentially of essentially linear ultrahigh molecular weight polyolefin which is essentially linear ultrahigh molecular weight polyethylene having an intrinsic viscosity of at least about 18 deciliters/gram, essentially linear ultrahigh molecular weight polypropylene having an intrinsic viscosity of at least about 6 deciliters/gram, or a mixture thereof, (b) finely divided particulate substantially water-insoluble filler, of which at least about 50 percent by weight is siliceous, distributed throughout the matrix, the filler constituting from about 50 percent to about 90 percent by weight of the microporous material, and (c) a network of interconnecting pores communicating throughout the microporous material, the pores constituting at leaast about 35 percent by volume of the microporous material, with a releasable active agent or precursor thereof to associate at least a portion of the releasable active agent or the precursor with at least a portion of the filler.

The releasable active agent is a substance or mixture of substances which, when delivered by the delivery device to the surrounding environment is useful for one or more purposes in the surrounding environment. Examples of such releasable active agents include, but are not limited to, flavors, fragrances (such as perfumes, scents, and the like), deodorizers, medicaments (such as drugs and the like), biocides (such as insecticides, herbicides, fungicides, and the like), antistatic agents, lubricants, corrosion inhibitors, preservatives, fertilizers, and dyes.

At least a portion of the active agent or precursor thereof is associated with at least a portion of the siliceous filler of the microporous material. The mechanism of the association may differ depending upon the nature of the active agent employed and the nature of the siliceous filler employed. Irrespective of the precise physical or chemical mechanism which prevails in a given situation, the association results from an interaction between the filler and the active agent or its precursor.

The releasable active agent or its precursor may be liquid, solid, or occasionally a gas. It may be in admixture with other substances which aid in placement of the releasable active agent or the precursor in the microporous material and/or assist in regulating the rate of release of the active agent from the microporous material. Solvents and fixatives are examples of such other substances.

Release of the active agent over a prolonged period of time may be due to any of a number of factors such as for example, volatilization, migration, diffusion, the breaking of physical or chemical bonds, or the reaction of one or more precursors to produce the releasable active agent in situ. The release may occur continuously as in the case of volatilization of liquid or solid, or it may be triggered by an external stimulus such as elevated temperature or absorption of catalyst or reactant into the microporous material. As an example of the last mechanism, a first precursor is introduced to the microporous material through one side and reacts within the microporous material with a second precursor already present in the microporous material to form an active agent which then proceeds out of the other side of the microporous material.

The tortuous pores of the microporous material provide resistance to diffusion or migration of active agent from the interior of the microporous material. In some cases this resistance is the principal mechanism providing for prolonged release of the active agent, while in others it is a secondary, but helpful, mechanism contributing to the prolonged release.

When desired, a reservoir of the releasable active agent or its precursor may be located on one side of the microporous material to replenish the microporous material with releasable active agent or precursor as releasable active agent is released from the microporous material or as precursor is consumed.

Inasmuch as ultrahigh molecular weight (UHMW) polyolefin is not a thermoset polymer having an infinite molecular weight, it is technically classified as a thermoplastic. However, because the molecules are essentially very long chains, UHMW polyolefin, and especially UHMW polyethylene, softens when heated but does not flow as a molten liquid in a normal thermoplastic manner. The very long chains and the peculiar properties they provide to UHMW polyolefin are believed to contribute in large measure to the desirable properties of the microporous material.

As indicated earlier, the intrinsic viscosity of the UHMW polyethylene is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 18 to about 39 deciliters/gram. An intrinsic viscosity in the range of from about 18 to about 32 deciliters/gram is preferred.

Also as indicated earlier the intrinsic viscosity of the UHMW polypropylene is at least about 6 deciliters/gram. In many cases the intrinsic viscosity is at least about 7 deciliters/gram. Although there is no particular restriction on the upper limit of the intrinsic viscosity, the intrinsic viscosity is often in the range of from about 6 to about 18 deciliters/gram. An intrinsic viscosity in the range of from about 7 to about 16 deciliters/gram is preferred.

As used herein and in the claims, intrinsic viscosity is determined by extrapolating to zero concentration the reduced viscosities or the inherent viscosities of several dilute solutions of the UHMW polyolefin where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMW polyolefin are ascertained from relative viscosities obtained at 135° C. using an Ubbelohde No. 1 viscometer in accordance with the general procedure of ASTM D 4020-81, except that several dilute solutions of differing concentration are employed. ASTM D 4020-81 is, in its entirety, incorporated herein by reference.

The nominal molecular weight of UHMW polyethylene is empirically related to the intrinsic viscosity of the polymer according to the equation:

$$M = 5.37 \times 10^4 [\eta]^{1.37}$$

where M is the nominal molecular weight and $[\eta]$ is the intrinsic viscosity of the UHMW polyethylene expressed in deciliters/gram. Similarly, the nominal molecular weight of UHMW polypropylene is empirically related to the intrinsic viscosity of the polymer according to the equation:

$$M = 8.88 \times 10^4 [\eta]^{1.25}$$

where M is the nominal molecular weight and $[\eta]$ is the intrinsic viscosity of the UHMW polypropylene expressed in deciliters/gram.

The essentially linear ultrahigh molecular weight polypropylene is most frequently essentially linear ultrahigh molecular weight isotactic polypropylene. Often the degree of isotacticity of such polymer is at least about 95 percent, while preferably it is at least about 98 percent.

Sufficient UHMW polyolefin should be present in the matrix to provide its properties to the microporous material. Other thermoplastic organic polymer may also be present in the matrix so long as its presence does not materially affect the properties of the microporous material in an adverse manner. The amount of the other thermoplastic polymer which may be present depends upon the nature of such polymer. In general, a greater amount of other thermoplastic organic polymer may be used if the molecular structure contains little branching, few long sidechains, and few bulky side groups, than when there is a large amount of branching, many long sidechains, or many bulky side groups. For this reason, the preferred thermoplastic organic polymers which may optionally be present are low density polyethylene, high density polyethylene, poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc, or the like. It is our experience that usually at least about 50 percent UHMW polyolefin, based on the weight of the matrix, will provide the desired properties to the microporous material. Often at least about 70 percent by weight of the matrix is UHMW polyolefin. In many cases, however, the other thermoplastic organic polymer is substantially absent.

The finely divided substantially water-insoluble siliceous filler used in the present invention is particulate. As present in the microporous material, the siliceous filler may be in the form of ultimate particles, aggregates of ultimate particles, or a combination of both. In most cases, at least about 90 percent by weight of the siliceous filler used in preparing the microporous material has gross particle sizes in the range of from about 5 to about 40 micrometers as determined by use of a Model TAII Coulter counter (Coulter Electronics, Inc.) according to ASTM C 690-80 but modified by stirring the filler for 10 minutes uin Isoton II electrolyte (Curtin Matheson Scientific, Inc.) using a four-blade, 4.445 centimeter diameter propeller stirrer. Preferably at least about 90 percent by weight of the siliceous filler has gross particle sizes in the range of from about 10 to about 30 micrometers. It is expected that the sizes of filler agglomerates will be reduced during processing of the ingredients to prepare the microporous material. Accordingly, the distribution of gross particle sizes in the microporous material may be smaller than in the raw filler itself. ASTM C 690-80 is, in its entirety, incorporated herein by reference.

Examples of suitable siliceous fillers include silica, mica, montmorillonite, kaolinite, asbestos, talc, diatomaceous earth, vermiculite, natural and synthetic zeolites, cement, calcium silicate, aluminum silicate, sodium aluminum silicate, aluminum polysilicate, alumina silica gels, and glass particles. Silica and the clays are the preferred siliceous fillers. Of the silicas, precipitated silica, silica gel, or fumed silica is most often used.

In addition to the siliceous filler, finely divided particulate substantially water-insoluble non-siliceous fillers may also be employed. Examples of such optional non-siliceous fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, magnesium carbonate, magnesium hydroxide, and finely divided particulate substantially water-insoluble flame retardant filler such as ethylenebis(tetrabromophthalimide), octabromodiphenyl oxide, decabromodiphenyl oxide, and ethylenebisdibromonorbornane dicarboximide.

The finely divided substantially water-insoluble non-siliceous filler used in the present invention is particulate. As present in the microporous material, the non-siliceous filler may be in the form of ultimate particles, aggregates of ultimate particles, or a combination of both. In most cases, at least about 75 percent by weight of the non-siliceous filler used in preparing the microporous material has gross particle sizes in the ranges of from about 0.1 to about 40 micrometers as determined by use of a Micromeretics Sedigraph 5000-D (Micromeretics Instrument Corp.) in accordance with the accompanying operating manual. The preferred ranges vary from filler to filler. For example, it is preferred that at least about 75 percent by weight of antimony oxide particles be in the range of from about 0.1 to about 3 micrometers, whereas it is preferred that at least about 75 percent by weight of barium sulfate particles be in the range of from about 1 to about 25 micrometers. It is expected that the sizes of filler agglomerates will be reduced during processing of the ingredients to prepare the microporous material. Therefore, the distribution of gross particle sizes in the microporous material may be smaller than in the raw non-siliceous filler itself.

The particularly preferred finely divided particulate substantially water-insoluble siliceous filler is precipitated silica. Although both are silicas, it is important to distinguish precipitated silica from silica gel inasmuch as these different materials have different properties. Reference in this regard is made to R. K. Iler, *The Chemistry of Silica*, John Wiley & Sons, New York (1979), Library of Congress Catalog No. QD 181.S6144, the entire disclosure of which is incorporated herein by reference. Note especially pages 15–29, 172–176, 218–233, 364–365, 462–465, 554–564, and 578–579. Silica gel is usually produced commercially at low pH by acidifying an aqueous solution of a soluble metal silicate, typically sodium silicate, with acid. The acid employed is generally a strong mineral acid such as sulfuric acid or hydrochloric acid although carbon dioxide is sometimes used. Inasmuch as there is essentially no difference in density between gel phase and the surrounding liquid phase while the viscosity is low, the gel phase does not settle out, that is to say, it does not precipitate. Silica gel, then, may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the the order of 100 parts of water per part of silica by weight, although the highly hydrated forms are only rarely used in the present invention.

Precipitated silica is usually produced commercially by combining an aqueous solution of a soluble metal silicate, ordinarily alkali metal silicate such as sodium silicate, and an acid so that colloidal particles will grow in weakly alkaline solution and be coagulated by the alkali metal ions of the resulting soluble alkali metal salt. Various acids may be used, including the mineral acids and carbon dioxide. In the absence of a coagulant, silica is not precipitated from solution at any pH. The coagulant used to effect precipitation may be the soluble alkali metal salt produced during formation of the colloidal silica particles, it may be added electrolyte such as a soluble inorganic or organic salt, or it may be a combination of both.

Precipitated silica, then, may be described as precipitated aggregates of ultimate particles of colloidal amorphous silica that have not at any point existed as macroscopic gel during the preparation. The sizes of the aggregates and the degree of hydration may vary widely.

Precipitated silica powders differ from silica gels that have been pulverized in ordinarily having a more open structure, that is, a higher specific pore volume. However, the specific surface area of precipitated silica as measured by the Brunauer, Emmet, Teller (BET) method using nitrogen as the adsorbate, is often lower than that of silica gel.

Many different precipitated silicas may be employed in the present invention, but the preferred precipitated silicas are those obtained by precipitation from an aqueous solution of sodium silicate using a suitable acid such as sulfuric acid, hydrochloric acid, or carbon dioxide. Such precipitated silicas are themselves known and processes for producing them are described in detail in U.S. Pat. No. 2,940,830, and in U.S. Pat. No. 4,681,750, The entire disclosures of which are incorporated herein by reference, including especially the processes for making precipitated silicas and the properties of the products.

In the case of the preferred filler, precipitated silica, the average ultimate particle size (irrespective of whether or not the ultimate particles are agglomerated) is less than about 0.1 micrometer as determined by transmission electron microscopy. Often the average ultimate particle size is less than about 0.05 micrometer. Preferably the average ultimate particle size of the precipitated silica is less than about 0.03 micrometer.

The finely divided particulate substatially water-insoluble filler constitutes from about 50 to 90 percent by weight of the microporous material. Frequently such filler constitutes from about 50 to about 85 percent by weight of the microporous material. From about 60 percent to about 80 percent by weight is preferred.

At least about 50 percent by weight of the finely divided particulate substantially water-insoluble filler is finely divided particulate substantially water-insoluble siliceous filler. In many cases at least about 65 percent by weight of the finely divided particulate substantially water-insoluble filler is siliceous. Often at least about 75 percent by weight of the finely divided particulate substantially water-insoluble filler is siliceous. Frequently at least about 85 percent by weight of the finely divided particulate water-insoluble filler is siliceous. In many instances all of the finely divided particulate water-insoluble filler is siliceous.

Minor amounts, usually less than about 5 percent by weight, of other materials used in processing such as lubricant, processing plasticizer, organic extraction liquid, surfactant, water, and the like, may optionally also be present. Yet other materials introduced for particular purposes may optionally be present in the microporous material in small amounts, usually less than about 15 percent by weight. Examples of such materials include antioxidants, ultraviolet light absorbers, dyes, pigments, and the like. The balance of the microporous material, exclusive of filler and any impregnant applied for one or more special purposes is essentially the thermoplastic organic polymer.

On an impregnant-free basis, pores constitute at least about 35 percent by volume of the microporous material. In many instances the pores constitute at least about 60 percent by volume of the microporous material. Often the pores constitute from at least about 35 percent to about 95 percent by volume of the microporous material. From about 60 percent to about 75 percent by volume is preferred. As used herein and in the claims, the porosity (also known as void volume) of the microporous material, expressed as percent by volume, is determined according to the equation:

$$\text{Porosity} = 100[1 - d_1/d_2]$$

where $d_1$ is the density of the sample which is determined from the sample weight and the sample volume as ascertained from measurements of the sample dimensions and $d_2$ is the density of the solid portion of the sample which is determined from the sample weight and the volume of the solid portion of the sample. The volume of the solid portion of the same is determined using a Quantachrome stereopycnometer (Quantachrome Corp.) in accordance with the accompanying operating manual.

The volume average diameter of the pores of the microporous material is determined by mercury porosimetry using an Autoscan mercury porosimeter (Quantachrome Corp.) in accordance with the accompanying operating manual. The volume average pore radius for a single scan is automatically determined by the porosimeter. In operating the porosimeter, a scan is made in the high pressure range (from about 138 kilopascals absolute to about 227 megapascals absolute). If about 2 percent or less of the total intruded volume occurs at the low end (from about 138 to about 250 kilopascals absolute) of the high pressure range, the volume average pore diameter is taken as twice the volume average pore radius determined by the porosimeter. Otherwise, an additional scan is made in the low pressure range (from about 7 to about 165 kilopascals absolute) and the volume average pore diameter is calculated according to the equation:

$$d = 2\left(\frac{v_1 r_1}{w_1} + \frac{v_2 r_2}{w_2}\right) \bigg/ \left(\frac{v_1}{w_1} + \frac{v_2}{w_2}\right)$$

where d is the volume average pore diameter, $v_1$ is the total volume of mercury intruded in the high pressure range, $v_2$ is the total volume of mercury intruded in the low pressure range, $r_1$ is the volume average pore radius determined from the high pressure scan, $r_2$ is the volume average pore radius determined from the low pressure scan, $w_1$ is the weight of the sample subjected to the high pressure scan, and $w_2$ is the weight of the sample subjected to the low pressures scan. Generally the volume average diameter of the pores is in the range of from about 0.02 to about 50 micrometers. Very often the volume average diameter of the pores is in the range of from about 0.04 to about 40 micrometers. From about 0.05 to about 30 micrometers is preferred.

In the course of determining the volume average pore diameter of the above procedure, the maximum pore radius detected is sometimes noted. This is taken from the low pressure range scan if run; otherwise it is taken from the high pressure range scan. The maximum pore diameter is twice the maximum pore radius.

Microporous material may be produced according to the general principles and procedures of U.S. Pat. No. 3,351,495, the entire disclosure of which is incorporated herein by reference, including especially the processes for making microporous materials and the properties of the products.

Preferably filler, thermoplastic organic polymer powder, processing plasticizer and minor amounts of lubricant and antioxidant are mixed until a substantially uniform mixture is obtained. The weight ratio of filler to polymer powder employed in forming the mixture is essentially the same as that of the microporous material to be produced. The mixture, together with additional processing plasticizer, is introduced to the heated barrel of a screw extruder. Attached to the extruder is a sheeting die. A continuous sheet formed by the die is forwarded without drawing to a pair of heated calender rolls acting cooperatively to form continuous sheet of lesser thickness than the continuous sheet exiting from the die. The continuous sheet from the calender then passes to a first extraction zone where the processing plasticizer is substantially removed by extraction with an organic liquid which is a good solvent for the processing plasticizer, a poor solvent for the organic polymer, and more volatile than the processing plasticizer. Usually, but not necessarily, both the processing plasticizer and the organic extraction liquid are substantially immiscible with water. The continuous sheet then passes to a second extraction zone where the residual organic extraction liquid is substantially removed by steam and/or water. The continuous sheet is then passed through a forced air dryer for substantial removal of residual water and remaining residual organic extraction liquid. From the dryer the continuous sheet, which is microporous material, is passed to a take-up roll.

The processing plasticizer has little solvating effect on the thermoplastic organic polymer at 60° C., only a moderate solvating effect at elevated temperatures on the order of about 100° C., and a significant solvating effect at elevated temperatures on the order of about 200° C. It is a liquid at room temperature and usually it is processing oil such as paraffinic oil, naphthenic oil, or aromatic oil. Suitable processing oils include those meeting the requirements of ASTM D 2226-82, Types 103 and 104. Preferred are those oils which have a pour point of less than 22° C. according to ASTM D 97-66 (reapproved 1978). Particularly preferred are oils having a pour point of less than 10° C. Examples of suitable oils include Shellflex® 412 and Shellflex® 371 oil (Shell Oil Co.) which are solvent refined and hydrotreated oils derived from naphthenic crude. ASTM D 2226-82 and ASTM D 97-66 (reapproved 1978) are, in their entireties, incorporated herein by reference. It is expected that other materials, including the phthalate ester plasticizers such as dibutyl phthalate, bis(2-ethylhexyl) phthalate, diisodecyl phthalate, dicyclohexyl phthalate, butyl benzyl phthalate, and ditridecyl phthalate will function satisfactorily as processing plasticizers.

There are many organic extraction liquids that can be used. Examples of suitable organic extraction liquids include 1,1,2-trichloroethylene, perchloroethylene, 1,2-dichloroethane, 1,1,1-trichloroethane, 1,1,2-trichloroethane, methylene chloride, chloroform, 1,1,2-trichloro-1,2,2-trifluoroethane, isopropyl alcohol, diethyl ether and acetone.

In the above described process for producing microporous material, extrusion and calendering are facilitated when the substantially water-insoluble filler carries much of the processing plasticizer. The capacity of the filler particles to absorb and hold the processing plasticizer is a function of the surface area of the filler. It is therefore preferred that the filler have a high surface area. High surface area fillers are materials of very small particle size, materials having a high degree of porosity or materials exhibiting both characteristics. Usually the surface area of the filler itself is in the range of from about 20 to about 400 square meters per gram as determined by the Brunauer, Emmett, Teller (BET) method according to ASTM C 819-77 using nitrogen as the adsorbate but modified by outgassing the system and the sample for one hour at 130° C. Preferably the surface area is in the range of from about 25 to 350 square meters per gram. ASTM C 819-77 is, in its entirety, incorporated herein by reference.

Inasmuch as it is desirable to essentially retain the filler in the microporous material, it is preferred that the substantially water-insoluble filler be substantially insoluble in the processing plasticizer and substantially insoluble in the organic extraction liquid when microporous material is produced by the above process.

The residual processing plasticizer content is usually less than 5 percent by weight of the microporous sheet and this may be reduced even further by additional extractions using the same or a different organic extraction liquid.

Pores constitute from about 35 to about 80 percent by volume of the microporous material when made by the above-described process. In many cases the pores constitute from about 60 to about 75 percent by volume of the microporous material.

The volume average diameter of the pores of the microporous material when made by the above-described process, is usually in the range of from about 0.02 to about 0.5 micrometers. Frequently the average diameter of the pores is in the range of from about 0.04 to about 0.3 micrometers. From about 0.05 to about 0.25 micrometers is preferred.

The microporous material produced by the above-described process may be used for producing articles of the present invention. However, it may optionally be stretched and the stretched microporous material used for producing such articles. When such stretching is employed, the product of the above-described process may be regarded as an intermediate product.

It will be appreciated that the stretching both increases the void volume of the material and induces regions of molecular orientation in the ultrahigh molecular weight (UHMW) polyolefin. As is well known in the art, many of the physical properties of molecularly oriented thermoplastic organic polymer, including tensile strength, tensile modulus, Young's modulus, and others, differ considerably from those of the corresponding thermoplastic organic polymer having little or no molecular orientation. Although it is not desired to be bound by any theory, it is believed that the properties of the UHMW polyolefin, the regions of molecular orientation, the high levels of filler loading, and the high degrees of porosity cooperate to provide many of the desirable properties characteristic of the stretched microporous material used in the present invention.

Stretched microporous material may be produced by stretching the intermediate product in at least one stretching direction above the elastic limit. Usually the stretch ratio is at least about 1.5. In many cases the stretch ratio is at least about 1.7. Preferably it is at least about 2. Frequently the stretch ratio is in the range of from about 1.5 to about 15. Often the stretch ratio is in the range of from about 1.7 to about 10. Preferably the stretch ratio is in the range of from about 2 to about 6. As used herein, the stretch ratio is determined by the formula:

$$S = L_2/L_1$$

where S is the stretch ratio, $L_1$ is the distance between two reference points located on the intermediate product and on a line parallel to the stretching direction, and $L_2$ is the distance between the same two reference points located on the stretched microporous material.

The temperatures at which stretching is accomplished may vary widely. Stretching may be accomplished at about ambient room temperature, but usually elevated temperatures are employed. The intermediate product may be heated by any of a wide variety of techniques prior to, during, and/or after stretching. Examples of these techniques include radiative heating such as that provided by electrically heated or gas fired infrared heaters, convective heating such as that provided by recirculating hot air, and conductive heating such as that provided by contact with heated rolls. The temperatures which are measured for temperature control purposes may vary according to the apparatus used and personal preference. For example, temperature-measuring devices may be placed to ascertain the temperatures of the surfaces of infrared heaters, the interiors of infrared heaters, the air temperatures of points between the infrared heaters and the intermediate product, the temperatures of the circulating hot air at points within the apparatus, the temperature of hot air entering or leaving the apparatus, the temperatures of the surfaces of rolls used in the stretching process, the temperature of heat transfer fluid entering or leaving such rolls, or film surface temperatures. In general, the temperature or temperatures are controlled such that the intermediate product is stretched about evenly so that the variations, if any, in film thickness of the stretched microporous material are within acceptable limits and so that the amount of stretched microporous material outside of those limits is acceptably low. It will be apparent that the temperatures used for control purposes may or may not be close to those of the intermediate product itself since they depend upon the nature of the apparatus used, the locations of the temperature-measuring devices, and the identities of the substances or objects whose temperatures are being measured.

In view of the locations of the heating devices and the line speeds usually employed during stretching, gradients of varying temperatures may or may not be present through the thickness of the intermediate product. Also because of such line speeds, it is impracticable to measure these temperature gradients. The presence of gradients of varying temperatures, when they occur, makes it unreasonable to refer to a singular film temperature. Accordingly, film surface temperatures, which can be measured, are best used for characterizing the thermal condition of the intermediate product. These are ordinarily about the same across the width of the intermediate product during stretching although they may be intentionally varied, as for example, to compensate for intermediate product having a wedge-shaped cross-section across the sheet. Film surface temperatures along the length of the sheet may be about the same or they may be different during stretching.

The film surface temperatures at which stretching is accomplished may vary widely, but in general they are such that the intermediate product is stretched about evenly, as explained above. In most cases, the film surface temperatures during stretching are in the range of form about 20° C. to about 220° C. Often such temperatures are in the range of from about 50° C. to about 200° C. From about 75° C. to about 180° C. is preferred.

Stretching may be accomplished in a single step or a plurality of steps as desired. For example, when the intermediate product is to be stretched in a single direction (uniaxial stretching), the stretching may be accomplished by a single stretching step or a sequence of stretching steps until the desired final stretch ratio is attained. Similarly, when the intermediate product is to be stretched in two directions (biaxial stretching), the stretching can be conducted by a single biaxial stretching step or a sequence of biaxial stretching steps until the desired final stretch ratios are attained. Biaxial stretching may also be accomplished by a sequence of one of more uniaxial stretching steps in one direction and one or more uniaxial stretching steps in another direction. Biaxial stretching steps where the intermediate product is stretched simultaneously in two directions and uniaxial stretching steps may be conducted in sequence in any order. Stretching in more than two directions is within contemplation. It may be seen that the various permutations of steps are quite numerous. Other steps, such as cooling, heating, sintering, annealing, reeling, unreeling, and the like, may optionally be included in the overall process as desired.

Various types of stretching apparatus are well known and may be used to accomplish stretching of the intermediate product. Uniaxial stretching is usually accomplished by stretching between two rollers wherein the second or downstream roller rotates at a greater peripheral speed than the first or upstream roller. Uniaxial stretching can also be accomplished on a standard tentering machine. Biaxial stretching may be accomplished by simultaneously stretching in two different directions on a tentering machine. More commonly, however, biaxial stretching is accomplished by first uniaxially stretching between two differentially rotating rollers as described above, followed by either uniaxially stretching in a different direction using a tenter machine or by biaxially stretching using a tenter machine. The most common type of biaxial stretching is where the two stretching directions are approximately at right angles to each other. In most cases where continuous sheet is being stretched, one stretching direction is at least approximately parallel to the long axis of the sheet (machine direction) and the other stretching direction is at least approximately perpendicular to the machine direction and is in the plane of the sheet (transverse direction).

After stretching has been accomplished, the microporous material may optionally be sintered, annealed, heat set and/or otherwise heat treated. During these optional steps, the stretched microporous material is usually held under tension so that it will not markedly shrink at the elevated temperatures employed, although some relaxation amounting to a small fraction of the maximum stretch ratio is frequently permitted.

Following stretching and any heat treatments employed, tension is released from the stretched microporous material after the microporous material has been brought to a temperature at which, except for a small amount of elastic recovery amounting to a small fraction of the stretch ratio, it is essentially dimensionally stable in the absence of tension. Elastic recovery under these conditions usually does not amount to more than about 10 percent of the stretch ratio.

The stretched microporous material may then be further processed as desired. Examples of such further processing steps include reeling, cutting, stacking, treatment to remove residual processing plasticizer or extraction solvent, and fabrication into shapes for various end uses.

In all cases, the porosity of the stretched microporous material is, unless impregnated after stretching, greater than that of the intermediate product. On an impregnant-free basis, pores usually constitute more than 80 percent by volume of the stretched microporous material. In many instances the pores constitute at least about 85 percent by volume of the stretched microporous material. Often the pores constitute from more than 80 percent to about 95 percent by volume of the stretched microporous material. From about 85 percent to about 95 percent by volume is preferred.

Generally the volume average diameter of the pores of the stretched microporous material is in the range of from 0.6 to about 50 micrometers. Very often the volume average diameter of the pores is in the range of from about 1 to about 40 micrometers. From about 2 to about 30 micrometers is preferred.

The microporous material, whether or not stretched, may be printed with a wide variety of printing inks using a wide variety of printing processes. Both the printing inks and the printing processes are themselves conventional.

There are many advantages in using the microporous material described herein as a printing substrate.

One such advantage is that the substrate need not be pretreated with any of the pretreatments customarily used to improve adhesion between the printing ink and polyolefin substrate such as flame treatment, chlorination, or especially corona discharge treatment which is most commonly employed. This is surprising inasmuch as untreated polyolefins such as polyethylene and polypropylene cannot ordinarily be successfully printed because of a lack of adhesion between the polyolefin printing ink and the polyolefin substrate. The microporous material substrates used in the present invention may be pretreated to further improve ink-substrate adhesion, but commercially satisfactory results can ordinarily be attained without employing such methods.

Another advantage is that the microporous material substrates accept a wide variety of printing inks, including most organic solvent-based inks which are incompatible with water, organic solvent-based inks which are compatible with water, and water-based inks.

Yet another advantage is very rapid drying of most inks to the tack-free state upon printing the microporous material substrates. This advantage is quite important in high speed press runs, in multicolor printing, and in reducing or even eliminating blocking of stacks or coils of the printed substrate.

A further advantage is the sharpness of the printed image that can be attained. This is especially important in graphic arts applications where fine lines, detailed drawings, or halftone images are to be printed. Halftone images printed on the microporous material substrates ordinarily exhibit high degrees of dot resolution.

Ink jet printing, especially when a water-based ink jet printing ink is used, is particularly suitable for printing bar codes on microporous material substrates. The resulting bars are sharp and of high resolution, which are important factors in reducing errors when the codes are read by conventional methods and equipment. The ink dries very rapidly when applied, thereby minimizing loss of bar resolution due to smearing in subsequent handling operations.

Printing processes, printing equipment, and printing inks have been extensively discussed and documented. Examples of reference works that may be consulted include L. M. Larsen, *Industrial Printing Ink*, Reinhold Publishing Corp., (1962); Kirk-Othmer, *Encyclopedia of Chemical Technology*, 2d Ed., John Wiley & Sons, Inc., Vol. 11, pages 611–632 (1966) and Vol. 16, pages 494–546 (1968); and R. N. Blair, *The Lithographers Manual*, The Graphic Arts Technical Foundation, Inc., 7th Ed. (1983).

For a more detailed description of printing on microporous material of the kind employed in the present invention, see U.S. Pat. No. 4,861,644, the entire disclosure of which is incorporated herein by reference.

The microporous material may be treated (such as by spraying, coating, impregnating, dipping, imbibing, the use of elevated pressure and/or vacuum to force liquid to the interior, and the like) with one or more substances which alter the transmission characteristics of the microporous material. The treatment, however, should not be carried out to the degree that the microporous material becomes impervious. For example, the rate of release of active agent may be reduced by treating the microporous material with any of various organic film-forming materials, of which many are well known, which effectively reduce the porosity of the microporous material. As another example, the microporous material may be treated with any of the various organic silanes or siloxanes to change the hydrophobic/hydrophilic or oleophobic/oleophilic characteristics of the microporous material and hence the active agent transmission rate.

The microporous material may be treated with releasable active agent or precursor thereof to associate at least a portion of the releasable active agent or the precursor with at least a portion of the filler. In most cases the material used to treat the microporous material is a liquid. The use of a liquid is preferred because it enhances association of the releasable active agent or its precursor with the filler. Solid active agent or precursor is frequently dissolved in volatile solvent or heated above its melting point and the resulting liquid used for treatment. Liquid active agent or precursor is often combined with volatile liquid carrier to assist in treatment and/or to act as a diluent to regulate the amount of active agent or precursor applied. The volatility of the solvent or other carrier is usually considerably greater than that of the active agent or precursor. Many techniques are known for treating porous or microporous substances with liquids and may be used to treat the microporous material in accordance with the present invention. Examples of such techniques include spraying, coating, impregnating, dipping, imbibing, the use of elevated pressure and/or vacuum to force liquid to the interior. Upon completion of the treatment, the microporous material may be essentially saturated with the liquid or, as is more usually the case, less than saturated. Volatile solvent or other volatile carrier, if present, may be removed by evaporation if desired.

In some cases the material used to treat the microporous material is a gas which becomes adsorbed on the filler. Treatment may be carried out by exposing the microporous material to the gas at the desired pressure which may be ambient atmospheric pressure, or above or below ambient atmospheric pressure. Usually the microporous material is degassed using vacuum and/or elevated temperatures before exposure to the gas.

The active agent delivery devices of the present invention have many and varied uses including shelf liners, drawer liners, animal litter, components of diapers and incontinence pads, and artificial flower petals which slowly release fragrance (including but not limited to perfume, scent and cologne) or deodorizer; strips, sheets, patches, or components of animal flea and tick collars which slowly release insecticide; strips, sheets, or patches which slowly release pheromone or other attractant; strips, sheets, or patches which, when placed in a laundry drier with wet clothing, slowly release fabric softener and/or antistatic agent; transdermal patches which, when placed in contact with the skin, slowly release medicament (including but not limited to one or more drugs); wraps which slowly release corrosion inhibitor to protect the article wrapped; lubricant devices which slowly release lubricant to protect delicate machinery, as for example mechanical clocks. These uses are only exemplary and it will be apparent that the active agent delivery devices of the present invention have a multitude of additional uses where controlled, sustained, or delayed release of active agent is advantageous.

The invention is further described in conjunction with the following examples which are to be considered illustrative rather than limiting.

EXAMPLES

Microporous Material Formation

The preparation of the above described materials is illustrated by the following descriptive examples. Processing oil was used as the processing plasticizer. Silica, polymer, lubricant and antioxidant in the amount specified in Table I were placed in a high intensity mixer and mixed at high speed for 30 seconds to thoroughly blend the dry ingredients. The processing oil needed to formulate the batch was pumped into the mixer over a period of 2-3 minutes with low speed agitation. After the completion of the processing oil addition a 2 minute low speed mix period was used to distribute the processing oil uniformly throughout the mixture.

TABLE I

| Example No. | \multicolumn{9}{c}{Formulations} | | | | | | | | |
| --- | --- | --- | --- | --- | --- | --- | --- | --- | --- |
| | 1 | 2 | 3 | 4 | 5 | 6 | 7 | 8 | 9 |
| Ingredient | | | | | | | | | |
| UHMWPE (1), kg | 5.67 | 9.98 | 4.25 | 8.57 | 6.12 | 9.98 | 3.49 | 5.73 | 11.84 |
| Polypropylene (2), kg | 0 | 0 | 1.42 | 0 | 0 | 0 | 0 | 0 | 0 |
| Precipitated Silica (3), kg | 19.96 | 19.96 | 19.96 | 19.96 | 13.02 | 9.98 | 19.96 | 20.17 | 20.87 |
| Silica Gel, kg | 0 | 0 | 0 | 0 | 6.49 | 0 | 0 | 0 | 0 |
| Clay, kg | 0 | 0 | 0 | 9.98 | 0 | 0 | 0 | 0 | 0 |
| Lubricant (4), g | 100 | 100 | 100 | 100 | 100 | 50 | 100 | 100 | 100 |
| Antioxidant (5), g | 100 | 100 | 100 | 100 | 100 | 50 | 100 | 100 | 100 |
| Processing Oil (6), kg in Batch | 31.21 | 31.21 | 31.21 | 37.58 | 33.44 | 16.89 | 31.72 | 31.29 | 34.13 |

TABLE I-continued

| | Formulations | | | | | | | | |
|---|---|---|---|---|---|---|---|---|---|
| Example No. | 1 | 2 | 3 | 4 | 5 | 6 | 7 | 8 | 9 |
| at Extruder | 13.61 | 41.59 | 30.39 | 28.60 | ~14 | 18.72 | 13.61 | ~10.96 | ~51.93 |

(1) UHMWPE = Ultrahigh Molecular Weight Polyethylene, Himont 1900, Himont, U.S.A., Inc.
(2) Profax ® 6801, Himont U.S.A., Inc.
(3) HiSil ® SBG, PPG Industries, Inc.
(4) Petrac ® CZ81, Desoto, Inc., Chemical Speciality Division
(5) Irganox ® B-215, Ciba-Geigy Corp.
(6) Shellflex ® 412, Shell Chemical Co.

The batch was then conveyed to a ribbon blender where usually it was mixed with up to two additional batches of the same composition. Material was fed from the ribbon blender to a twin screw extruder by a variable rate screw feeder. Additional processing oil was added via a metering pump into the feed throat of the extruder. The extruder mixed and melted the formulation and extruded it through a 76.2 centimeter×0.3175 centimeter slot die. The extruded sheet was then calendered. A description of one type of calender that may be used may be found in the U.S. Pat. No. 4,734,229, the entire disclosure of which is incorporated herein by reference, including the structures of the devices and their modes of operation. Other calenders of different design may alternatively be used; such calenders and their modes of operation are well known in the art. The hot, calendered sheet was then passed around a chill roll to cool the sheet. The rough edges of the cooled calendered sheet were trimmed by rotary knives to the desired width.

The oil filled sheet was conveyed to the extractor unit where it was contacted by both liquid and vaporized 1,1,2-trichloroethylene (TCE). The sheet was transported over a series of rollers in a serpentine fashion to provide multiple, sequential vapor/liquid/vapor contacts. The extraction liquid in the sump was maintained at a temperature of 65°–88° C. Overflow from the sump of the TCE extractor was returned to a still which recovered the TCE and the processing oil for reuse in the process. The bulk of the TCE was extracted from the sheet by steam as the sheet was passed through a second extractor unit. A description of these types of extractors may be found in European Patent Application Publication No. EP 0 191 615, the entire disclosure of which is incorporated herein by reference, including especially the structures of the devices and their modes of operation. The sheet was dried by radiant heat and convective air flow. The dried sheet was wound on cores to provide roll stock for further processing.

The microporous sheets, as well as the hereinafter described biaxially stretched microporous sheets produced therefrom, were tested for various physical properties. Table II identifies the properties with the methods used for their determination. The various ASTM test methods and Method 502 C, referenced in Table II, are, in their entireties, incorporated herein by reference. The results of physical testing of the unstretched microporous sheets are shown in Table III.

Property values indicated by MD (machine direction) were obtained on samples whose major axis was oriented along the length of the sheet. TD (transverse direction; cross machine direction) properties were obtained from samples whose major axis was oriented across the sheet.

TABLE II

Physical Test Methods

| Property | Test Method |
|---|---|
| Tensile Strength Elongation | ASTM D 412-83. |
| Porosity | As described in the text above. |
| Matrix Tensile Strength | Tensile Strength determined in accordance with ASTM D 412-83 multiplied by the quantity 100/(100-Porosity). |
| Tear Strength, Die C | ASTM D 624-81. |
| Processing Oil Content | Method 502 C in "Standard Methods for the Examination of Water and Wastewater", 14th Ed., APHA-AWWA-WPCF (1975). |
| Maximum Pore Diaster | Mercury Porosimetry, as described in the text above. |
| Volume Average Pore Diameter | Mercury Porosimetry, as described in the text above. |
| Gurley Air Flow | ASTM D 726-58 (reapproved 1971), Method A. |
| Mullens Hydrostatic Resistance | ASTM D 751-79, Sec. 30-34, Method A. |
| MVTR (Moisture Vapor Transmission Rate) | ASTM E 96-80. |
| Methanol Bubble Pressure | ASTM F 316-80, using methanol. |
| Maximum Limiting Pore Diameter | ASTM F316-80, using methanol where cy = 22.34 (μm)(kPa). |
| Heat Shrinkage | ASTM D 1204-84, using 15.24 cm x 20.32 cm sample, 1 hr at 100° C. |
| Strip Tensile Strength and Elongation | ASTM D 828-60. |
| Breaking Factor and Elongation | ASTM D 882-83. |

TALBE III

| | Physical Properties of Microporous Sheet | | | | | | | | |
|---|---|---|---|---|---|---|---|---|---|
| Example No. | 1 | 2 | 3 | 4 | 5 | 6 | 7 | 8 | 9 |
| Thickness, mm | 0.229 | 0.279 | 0.229 | 0.381 | 0.483 | 0.254 | 0.229 | 0.356 | 0.305 |
| Matrix Tensile Strength, MPa | | | | | | | | | |
| MD | 23.82 | 34.33 | 25.66 | 27.79 | 29.21 | 70.47 | 20.35 | 31.90 | 51.37 |
| TD | 9.94 | 14.91 | 10.38 | 19.05 | 15.55 | 26.39 | 5.97 | 15.82 | 21.25 |
| Elongation at break, % | | | | | | | | | |
| MD | 250 | 279 | 227 | | | 14 | 110 | 264 | |
| TD | 108 | 140 | 112 | 546 | 470 | 482 | 214 | 466 | |
| Tear Strength, kN/m | | | | | | | | | |
| MD | 36.25 | 61.47 | 47.81 | 56.39 | 57.09 | 93.34 | 24.52 | 53.06 | 87.04 |
| TD | 18.04 | 39.93 | 23.12 | 39.75 | 32.22 | 89.66 | 7.36 | 32.57 | 56.39 |
| Porosity, vol % | 71 | 66 | 68 | 57.9 | 59.3 | 58.9 | 77 | 66 | 66.9 |
| Processing Oil Content, wt % | 4.1 | 2.7 | 2.4 | | | | 2.7 | 2.4 | |
| Maximum Pore Diameter, μm | 0.86 | 0.30 | 0.28 | 1.34 | 6.11 | 0.16 | | | |
| Volume Average Pore Diameter, μm | 0.11 | 0.065 | 0.069 | 0.099 | 0.111 | 0.12 | | | |
| Gurley Air Flow, sec/100 cc | 904 | 1711 | 955 | | | 4098 | 422 | 1757 | 1792 |

Biaxial Stretching of Microporous Sheet

Portions of the microporous materials produced in Examples 1–3 and microporous material taken from a different roll of microporous material produced during the same production run as the microporous material of Example 8 were unwound from cores and biaxially stretched by first uniaxially stretching in the machine direction using a single stage roll-to-roll machine direction stretching (MDS) unit and then essentially uniaxially stretching in the transverse direction using a moving clip tenter frame as a transverse direction stretching (TDS) unit. A preheat roll was employed with the MDS unit to heat the sheet prior to stretching. In the TDS unit, the sheet was heated by infrared radiant heater. The Preheat and Stretch I Zones of the TDS unit each contained both upper and lower banks of such heaters. The upper banks were located about 10.16 centimeters above the intermediate product while the lower banks were located about 15.24 centimeters below the intermediate product. Electrical power to the heaters of each lower bank was controlled by an on-off controller in response to the difference between a set point and the signal provided by a thermocouple mounted in one heater of the bank. Autotransformers were used to adjust electrical power to the heaters of the upper banks. The Stretch II, Stretch III, Sinter I, and Sinter II Zones each contained upper banks of infrared radiant heaters located about 10.16 centimeters above the intermediate product. There were no lower banks in these zones. Electrical power to the heaters of each upper bank was controlled as described in respect of the heaters of each lower bank in the Preheat and Stretch I Zones. For a description of a typical TDS unit, see FIG. 2 and column 2, lines 43–69, of U.S. Pat. No. 2,823,421, the entire disclosure of which is incorporated herein by reference.

The MDS stretch ratio was varied by controlling the relative peripheral speeds of the feed rolls and the take-off rolls of the MDS unit. The chain track positions in the tenter frame were set to achieve the desired stretch ratio and then to essentially maintain that stretch ratio during sintering. For each of the Examples 10–31, the settings of one of the first four vertical columns under the heading "Approximate Transverse Stretch Ratio" in Table IV were employed. The correct column may be ascertained by matching up the TD stretch ratio of the example with the final stretch ratio of the column. For Examples 32 and 33, the settings of the fifth vertical column under the same heading in Table IV were employed.

TABLE IV

| | Transverse Direction Stretching | | | | | |
|---|---|---|---|---|---|---|
| Zone | Cumulative Distance from Beginning of Oven, meters | Approximate Transverse Stretch Ratio | | | | |
| Preheat | 0 | 1 | 1 | 1 | 1 | 1 |
| Stretch I | 2.794 | 1 | 1 | 1 | 1 | 1 |
| Stretch II | 4.318 | 1.33 | 1.44 | 1.65 | 1.87 | 1.45 |
| Stretch III | 8.890 | 2.31 | 2.75 | 3.62 | 4.49 | 2.95 |
| Sinter I | 9.779 | 2.5 | 3 | 4 | 5 | 3 |
| Sinter II | 11.430 | 2.5 | 3 | 4 | 5 | 3 |
| | 13.716 | 2.5 | 3 | 4 | 5 | 3 |

The microporous sheet stock of Examples 1–3 and microporous sheet stock taken from a different roll of microporous material produced during the same production run as the microporous material of Example 8 were fed over the preheat roll of the MDS unit which was heated to the temperature indicated in Tables V–VIII. The sheet was then stretched to the indicated stretch ratio by maintaining the relative peripheral speeds of the second and first stretch rolls at essentially the same ratio as the stretch ratio. The line speed given in Tables V–VIII is the output speed of the MDS unit and the machine direction speed of the TDS unit. The linear feed rate from the roll stock of microporous material to the MDS unit was set at a value given by the line speed divided by the MDS stretch ratio. Thus, with a line speed of 24 m/min and a MDS stretch ratio of 2, the linear feed rate from the roll stock of the MDS unit would be 12 m/min. The properties of several representative examples of biaxially stretched sheets are given in Tables V–VIII.

TABLE V

Properties of Biaxially Stretched Microporous Sheets Produced from Microporous Sheet of Example 1

| Example No. | 10 | 11 | 12 | 13 | 14 | 15 | 16 | 17 | 18 |
|---|---|---|---|---|---|---|---|---|---|
| Thickness, mm | 0.178 | 0.152 | 0.127 | 0.076 | 0.076 | 0.102 | 0.127 | 0.102 | 0.076 |
| Stretch Ratio | | | | | | | | | |
| MD | 2 | 2 | 2 | 2 | 3 | 3 | 3 | 3 | 3 |
| TD | 3 | 3 | 4 | 5 | 3 | 3 | 3 | 3 | 4 |
| Line Speed m/min | 48.8 | 24.4 | 24.4 | 24.4 | 24.4 | 24.4 | 24.4 | 24.4 | 24.4 |
| MDS Preheat Temp., °C. | 79 | 79 | 79 | 79 | 79 | 79 | 79 | 79 | 79 |
| TDS Average Zonal Set Point Temps.,°C. | 149 | 177 | 177 | 149 | 149 | 149 | 177 | 149 | 177 |
| Preheat (lower banks) | | | | | | | | | |
| Stretch I (lower Banks) | 149 | 177 | 177 | 149 | 149 | 149 | 177 | 149 | 177 |
| Stretch II | 189 | 171 | 171 | 189 | 189 | 189 | 171 | 189 | 171 |
| Stretch III | 149 | 142 | 142 | 149 | 149 | 149 | 142 | 149 | 142 |
| Sinter I | 149 | 144 | 144 | 149 | 149 | 149 | 144 | 149 | 144 |
| Sinter II | 204 | 227 | 227 | 204 | 149 | 204 | 227 | 260 | 227 |
| Weight, g/m$^2$ | 27 | 24 | 17 | 14 | 14 | 10 | 14 | 14 | 10 |
| Porosity, vol % | 91 | 90 | 92 | 90 | 89 | 93 | 93 | 93 | 91 |
| Matrix Tensile Strength, MPa | | | | | | | | | |
| MD | 53.70 | 32.96 | 40.25 | 25.30 | 29.52 | 62.74 | 67.77 | 41.96 | 56.69 |
| TD | 40.14 | 29.30 | 65.76 | 46.54 | 61.99 | 45.41 | 43.93 | 57.62 | 55.77 |
| Elongation at break, % | | | | | | | | | |
| MD | 57 | 56 | 60 | 67 | 26 | 23 | 34 | 18 | 33 |
| TD | 27 | 41 | 13 | 9 | 23 | 27 | 30 | 31 | 12 |
| Gurley Air Flow, sec/100 cc | 47 | 45 | 40 | 29 | 32 | 28 | 37 | 28 | 36 |
| Tear Strength, kN/m | | | | | | | | | |
| MD | 9.28 | 5.78 | 7.01 | 3.85 | 2.28 | 5.08 | 6.30 | 5.60 | 5.08 |
| TD | 4.90 | 4.90 | 7.01 | 8.23 | 7.53 | 1.93 | 4.38 | 4.55 | 4.73 |
| Mullens Hydrostatic, kPa | 483 | 434 | 490 | 448 | 476 | 503 | 496 | 434 | 510 |
| MVTR g/m$^2$ day | 935 | | | | | | | 963 | |
| Methanol Bubble Point Pressure, kPa | 290 | 276 | 296 | 234 | 145 | 276 | 324 | 55 | 317 |
| Maximum Limiting Pore Diameter, μm | 0.077 | 0.081 | 0.075 | 0.095 | 0.154 | 0.081 | 0.069 | 0.404 | 0.070 |
| Maximum Pore Diameter, μm | | | | | | | 155 | | |
| Volume Average Pore Diameter, μm | | | | | | | 17.92 | | |
| Heat Shrinkage after 1 hr at 100° C., % | | | | | | | | | |
| MD | 19.0 | | 9.4 | 12.0 | | 19.3 | 24.1 | 21.2 | |
| TD | 23.2 | | 22.5 | 28.3 | | 25.7 | 29.1 | 30.8 | |

The biaxially stretched microporous sheet of Example 16 was examined by scanning electron microscopy at a magnification of 430×. A section taken in a plane perpendicular to the sheet surface (viz., looking into the thickness) and along the machine direction showed substantial pore elongation. A section taken in a plane perpendicular to the sheet surface and along the transverse direction showed pore elongation which was not as pronounced as along the machine direction. A view of the sheet surface (not sectioned) showed that large void structures were not as numerous as in views of either of the sections looking into the thickness.

TABLE VI

Properties of Biaxially Stretched Microporous Sheets Produced from Microporous Sheet of Example 2

| Example No. | 19 | 20 | 21 | 22 | 23 | 24 | 25 | 26 | 27 |
|---|---|---|---|---|---|---|---|---|---|
| Thickness, mm | 0.203 | 0.152 | 0.178 | 0.127 | 0.152 | 0.127 | 0.102 | 0.076 | 0.178 |
| Stretch Ratio | | | | | | | | | |
| MD | 2 | 2 | 2 | 2 | 2 | 3 | 3 | 3 | 3 |
| TD | 2.5 | 3 | 3 | 3 | 4 | 3 | 3 | 3 | 4 |
| Line Speed | 24.4 | 24.4 | 15.2 | 24.4 | 15.2 | 24.4 | 15.2 | 24.4 | 15.2 |

TABLE VI-continued
Properties of Biaxially Stretched Microporous Sheets Produced from Microporous Sheet of Example 2

| Example No. | 19 | 20 | 21 | 22 | 23 | 24 | 25 | 26 | 27 |
|---|---|---|---|---|---|---|---|---|---|
| m/min |  |  |  |  |  |  |  |  |  |
| MDS Preheat Temp., °C. | 104 | 104 | 121 | 79 | 121 | 104 | 121 | 79 | 121 |
| TDS Average Zonal Set Point Temps.,°C. | 177 | 177 | 149 | 149 | 149 | 177 | 149 | 149 | 149 |
| Preheat (lower banks) |  |  |  |  |  |  |  |  |  |
| Stretch I (lower Banks) | 177 | 177 | 149 | 149 | 149 | 177 | 149 | 149 | 149 |
| Stretch II | 171 | 171 | 188 | 188 | 188 | 171 | 188 | 188 | 188 |
| Stretch III | 142 | 142 | 144 | 149 | 144 | 142 | 144 | 149 | 144 |
| Sinter I | 144 | 144 | 200 | 149 | 144 | 144 | 144 | 149 | 144 |
| Sinter II | 227 | 227 | 255 | 316 | 255 | 227 | 255 | 316 | 255 |
| Weight, g/m$^2$ | 44 | 24 |  |  | 24 | 17 |  | 14 | 31 |
| Porosity, vol % | 86 | 90 |  |  | 90 | 92 |  | 90 | 90 |
| Matrix Tensile Strength, MPa |  |  |  |  |  |  |  |  |  |
| MD | 52.94 | 61.50 |  |  | 36.61 | 96.18 |  | 73.91 | 37.51 |
| TD | 44.47 | 67.98 |  |  | 109.49 | 54.38 |  | 75.01 | 117.21 |
| Elongation at break, % |  |  |  |  |  |  |  |  |  |
| MD | 58 | 54 | 161 | 41 | 87 | 31 | 13 | 19 | 111 |
| TD | 51 | 39 | 15 | 16 | 9 | 42 | 16 | 16 | 7 |
| Tear Strength, kN/m |  |  |  |  |  |  |  |  |  |
| MD | 20.31 | 12.61 | 17.51 | 6.13 | 13.13 | 12.26 | 8.41 | 5.95 | 18.56 |
| TD | 13.31 | 12.78 | 21.02 | 7.18 | 11.03 | 9.11 | 5.25 | 7.53 | 19.44 |
| Gurley Air Flow, sec/100 cc | 81 | 40 |  |  | 46 | 45 |  |  | 52 |
| Mullens Hydrostatic, kPa | 745 | 689 | 676 | 496 | 745 | 717 | 641 | 503 | 703 |
| MVTR g/m$^2$ day |  |  | 868 | 761 |  | 947 | 913 | 827 |  |
| Methanol Bubble Point Pressure, kPa | 290 | 303 |  |  | 303 | 365 |  |  | 290 |
| Maximum Limiting Pore Diameter, μm | 0.077 | 0.074 |  |  | 0.074 | 0.061 |  |  | 0.077 |
| Maximum Pore Diameter, μm |  | 111 |  |  |  | >146 |  |  |  |
| Volume Average Pore Diameter, μm |  | 7.13 |  |  |  | 4.70 |  |  |  |
| Heat Shrinkage after 1 hr at 100° C., % |  |  |  |  |  |  |  |  |  |
| MD | 11.7 |  | 3.8 | 7.1 | 12.3 |  | 15.3 | 6.3 | 7.7 |
| TD | 24.4 |  | 23.6 | 11.8 | 22.0 |  | 34.1 | 18.9 | 21.5 |

The biaxially stretched microporous sheet of Example 24 was examined by scanning electron microscopy at a magnification of 430×. A section taken in a plane perpendicular to the sheet surface and along the transverse direction showed pore elongation which was not as pronounced as that seen in a similar section taken along the machine direction. A view of the sheet surface (not sectioned) showed that large void structures were not as numerous as in views of either of the sections looking into the thickness.

TABLE VII
Properties of Biaxially Stretched Microporous Sheets Produced from Microporous Sheet of Example 3

| Example No. | 28 | 29 | 30 | 31 |
|---|---|---|---|---|
| Thickness, mm | 0.178 | 0.102 | 0.127 | 0.102 |
| Stretch Ratio |  |  |  |  |
| MD | 2 | 2 | 3 | 3 |
| TD | 3 | 3 | 3 | 4 |
| Line Speed | 24.4 | 24.4 | 24.4 | 24.4 |
| m/min |  |  |  |  |
| MDS Preheat Temp., °C. | 79 | 79 | 79 | 79 |
| TDS Average Zonal Set Point Temps.,°C. | 177 | 149 | 177 | 177 |
| Preheat (lower banks) |  |  |  |  |
| Stretch I (lower Banks) | 177 | 149 | 177 | 177 |
| Stretch II | 171 | 188 | 171 | 171 |
| Stretch III | 142 | 149 | 142 | 142 |
| Sinter I | 144 | 149 | 144 | 144 |
| Sinter II | 227 | 260 | 227 | 227 |
| Weight, g/m$^2$ | 27 | 14 | 20 | 14 |
| Porosity, vol % | 90 | 91 | 90 | 92 |
| Matrix Tensile |  |  |  |  |

TABLE VII-continued

Properties of Biaxially Stretched Microporous Sheets Produced from Microporous Sheet of Example 3

| Example No. | 28 | 29 | 30 | 31 |
|---|---|---|---|---|
| Strength, MPa | | | | |
| MD | 29.58 | 52.94 | 77.84 | 109.89 |
| TD | 122.73 | 44.43 | 32.96 | 39.90 |
| Elongation at break, % | | | | |
| MD | 90 | 47 | 27 | 17 |
| TD | 9 | 24 | 32 | 30 |
| Tear Strength, kN/m | | | | |
| MD | 15.41 | 10.51 | 15.24 | 7.18 |
| TD | 21.02 | 5.43 | 4.20 | 3.50 |
| Gurley Air Flow, sec/100 cc | 56 | 33 | | 36 |
| Mullens Hydrostatic, kPa | 552 | 655 | 641 | 586 |
| MVTR g/m² day | 843 | 815 | 862 | 982 |
| Methanol Bubble Point Pressure, kPa | 303 | 276 | | 317 |
| Maximum Limiting Pore Diameter, μm | 0.074 | 0.081 | | 0.070 |
| Heat Shrinkage after 1 hr at 100° C., % | | | | |
| MD | 24.1 | 16.5 | 26.4 | |
| TD | 40.1 | 31.4 | 34.8 | |

TABLE VIII

Properties of Biaxially Stretched Microporous Sheets Produced from Microporous Sheet Similar to that of Example 8

| Example No. | 32 | 33 |
|---|---|---|
| Thickness, mm | 0.160 | 0.165 |
| Stretch Ratio | | |
| MD | 2 | 3 |
| TD | 3 | 3 |
| Line Speed m/min | 15.5 | 15.54 |
| MDS Preheat Temp., °C. | 93 | 93 |
| TDS Average Zonal Set Point Temps.,°C. | 232 | 232 |
| Preheat (lower banks) | | |
| Stretch I (lower Banks) | 149 | 149 |
| Stretch II | 204 | 204 |
| Stretch III | 127 | 149 |
| Sinter I | 149 | 149 |
| Sinter II | 149 | 149 |
| Weight, g/m² | 19.7 | 19.3 |
| Porosity, vol % | 91.6 | 92.5 |
| Matrix Tensile Strength, MPa | | |
| MD | 52.63 | 80.80 |
| TD | 24.53 | 23.62 |
| Elongation at break, % | | |
| MD | 29.7 | 14.3 |
| TD | 24.4 | 29.2 |
| Tear Strength, kN/m | | |
| MD | 53.06 | 46.58 |
| TD | 32.57 | 33.62 |
| Gurley Air Flow, sec/100 cc | 25 | 18 |
| Mullens Hydrostatic, kPa | 345 | 359 |
| MVTR g/m² day | 1004 | 928 |
| Methanol Bubble Point Pressure, kPa | 165 | 159 |
| Maximum Limiting Pore Diameter, μm | 0.135 | 0.141 |

Microporous Material Formation

Larger batch mixing equipment was employed than was used for Examples 1–9. Processing oil was used as the processing plasticizer. Silica, polymer, lubricant, and antioxidant in the amount specified in Table IX were placed in a high intensity mixer and mixed at high speed for 6 minutes. The processing oil needed to formulate the batch was pumped into the mixer over a period of 12–18 minutes with high speed agitation. After completion of the processing oil addition a 6 minute high speed mix period was used to complete the distribution of the processing oil uniformly throughout the mixture.

TABLE IX

| | Formulations | | |
|---|---|---|---|
| Example No. | 34 | 35 | 36 |
| Ingredient | | | |
| UHMWPE (1), kg | 24.04 | 17.24 | 17.24 |
| HDPE (2), kg | 0.00 | 6.80 | 6.80 |
| Precipitated Silica (3), kg | 59.87 | 59.87 | 59.87 |
| Lubricant (4), g | 300.0 | 300.0 | 600.0 |
| Antioxidant (5), g | 300.0 | 300.0 | 0.0 |
| (6), g | 0.0 | 0.0 | 100.0 |
| Processing Oil (7), kg | | | |
| in Batch | 91.63 | 91.63 | 91.63 |
| at Extruder | ~35.14 | ~35.14 | ~35.14 |

(1) UHMWPE = Ultrahigh Molecular Weight Polyethylene, Himont 1900, Himont U.S.A., Inc.
(2) HDPE = High Density Polyethylene, Chevron 9690T, Chevron Chemical Co.
(3) HiSil ® SBG, PPG Industries, Inc.
(4) Petrac ® CZ81, Desoto, Inc., Chemical Speciality Division
(5) Irganox ® B-215, Ciba-Geigy Corp.
(6) Irganox ® 1010, Ciba-Geigy Corp.
(7) Shellflex ® 371, Shell Chemical Co.

The batch was then processed according to the general procedures described in respect of Examples 1–9 to form microporous sheets.

The microporous sheets, as well as the hereinafter described biaxially stretched microporous sheets produced therefrom, were tested for various physical properties. Table II identifies the properties with the methods used for their determination. The results of physical testing of the microporous sheets are shown in Table X. The abbreviations MD and TD have the same meanings previously discussed.

TABLE X

Physical Properties of Microporous Sheet

| Example No. | 34 | 35 | 36 |
|---|---|---|---|
| Thickness, mm | 0.267 | 0.254 | 0.255 |
| Strip Tensile Strength, kN/m | | | |
| MD | 3.42 | | |
| TD | 1.52 | | |
| Breaking Factor, kN/m | | | |

TABLE X-continued

| Physical Properties of Microporous Sheet | | | |
|---|---|---|---|
| Example No. | 34 | 35 | 36 |
| MD | | 3.44 | 3.23 |
| TD | | 1.42 | 1.52 |
| Elongation at break, % | | | |
| MD | 391 | 477 | 688 |
| TD | 448 | 451 | 704 |
| Processing Oil Content, wt % | 2.8 | 3.3 | 3.1 |

Biaxial Stretching of Microporous Sheet

Portions of the microporous materials prouduced in Examples 34 and 35 were unwound from cores and biaxially stretched by first uniaxially stretching in the machine direction using a single stage roll-to-roll MDS unit and then essentially uniaxially stretching in the transverse direction using a moving clip tenter frame as a TDS unit.

Operation of the MDS unit can be characterized by the temperatures and line speeds shown in Table XI.

TABLE XI

| MDS Unit Parameters | | | | |
|---|---|---|---|---|
| Roll No. | Function | Diameter, mm | Temperature, °C. | Peripheral Speed, m/min |
| 1 | Preheat | 305 | 116 | 3.84 |
| 2 | Preheat | 305 | 116 | 3.84 |
| 3 | Stretching | 152 | 127 | 3.84 |
| 4 | Stretching | 152 | 127 | 11.52 |
| 5 | Annealing | 305 | 79 | 11.53 |
| 6 | Cooling | 305 | 38 | 11.53 |

The gap between the slow and fast stretching rolls (Rolls 3 and 4, respectively) was 0.533 millimeter.

The TDS unit was a typical chain and clip tentering frame machine. It comprised three contiguous heating zones, each 2.54 meters in length where the beginning of the first heating zone coincided with the entrance to the TDS unit. The microporous sheet was heated by recirculating hot air in the heating zones. The heating zone temperatures are indicated in Table XII, where heating zone numbers increase in the direction of sheet travel.

TABLE XII

| Heating Zone Temperature | |
|---|---|
| Heating Zone | Temperature, °C. |
| 1 | 107 |
| 2 | 116 |
| 3 | 121 |

Stretching was controlled by positioning the tracks in which the chains holding the gripping clips rode. Microporous sheets, which had been uniaxially stretched in the machine direction as described above, were introduced to the TDS unit which had the track geometry shown in Table XIII.

TABLE XIII

| Track Geometry of TDS Unit | |
|---|---|
| Distance from Entrance, meters | Width, meters |
| −0.30 | 0.53 |
| +1.22 | 0.53 |
| 2.01 | 0.53 |
| 2.74 | 0.74 |
| 3.51 | 0.97 |

TABLE XIII-continued

| Track Geometry of TDS Unit | |
|---|---|
| Distance from Entrance, meters | Width, meters |
| 4.27 | 1.17 |
| 5.03 | 1.38 |
| 5.79 | 1.60 |
| 7.32 | 1.60 |
| 7.92 | 1.57 |

The properties of representative samples of biaxially stretched microporous sheets are given in Table XIV.

TABLE XIV

| Properties of Biaxially Stretched Microporous Sheets | | |
|---|---|---|
| Example No. | 37 | 38 |
| Microporous Sheet Feedstock, Example No. | 34 | 35 |
| Thickness, mm | 0.228 | 0.250 |
| Stretch Ratio | | |
| MD | 3 | 3 |
| TD | 3 | 3 |
| Line Speed, m/min | 13.4 | 13.4 |
| Weight, g/m² | 19.67 | 21.56 |
| Porosity, vol % | 92.1 | 91.1 |
| Breaking Factor, kN/m | | |
| MD | 1.175 | 1.158 |
| TD | 0.716 | 0.412 |
| Elongation at break, % | | |
| MD | 41 | 39 |
| TD | 54 | 61 |
| Gurley Air Flow, sec/100 cc | 41 | 48 |
| Mullens Hydrostic, kPa | 600 | 579 |

EXAMPLE 39

A first solution was prepared by dissolving about 15 cubic centimeters of No. 7 Rose Pink RIT ® dye (CPC International, Inc.) in about 600 milliliters of water.

A second solution was prepared by adding 40 drops of No. 4001 Rose Petal fragrance (Chemia Corp.). and 20 drops of No. 3008 Rose fragrance (Chemia Corp.) to about 400 milliliters of absolute ethanol.

A dying and perfuming solution was prepared by admixing all of the first and second solutions.

A portion of biaxially stretched microporous sheet produced in accordance with the principles heretofore described was immersed in the above dying and perfuming solution at room temperature until the microporous material was dyed a light pink color. The dyed and perfumed microporous material was then removed from the dying and perfuming solution and allowed to dry. During immersion and/or drying, the microporous material shrunk slightly. The dry microporous material was gently stretched by hand both in the machine direction and in the transverse direction, but not so much as to restore it to the original dimensions.

A PRETTY PETALS ® No. 3R-30 Silky Sweetheart Rose artificial flower kit (Signaigo & Rossi, Inc., d.b.a. Sirocraft) was purchased. One of the tetrapetalous No. 3R rose cuts from the kit was used as a pattern from which a die was fabricated. The die was used to cut three identical tetrapetalous artificial petal elements from the above dyed and perfumed microporous material and a small hole was punched in the center of each. The artificial petals of each artificial petal element were stretched slightly over a large ball bearing to provide the gentle dish-shaped appearance characteristic of true rose petals. The tips of opposing petals were about 7.8 centimeters apart while the innermost points of opposing sinuses were about 1.8 centimeters apart.

A No. 717 white cotton mold from the kit comprised a generally teardrop-shaped mold head formed of cotton wrapped about a wire. The cotton was sized to increase firmness and to hold the cotton in place. The equator of the mold head is a narrow region encircling the surface of mold head at its largest cross-section perpendicular to the axis of symmetry. The diameter of the equator was about 1.6 centimeters while the length of the mold head along the axis of symmetry was about 2.0 centimeters. A band of white glue was placed on the mold head along the equator.

White glue was placed locally on both lateral regions of the slightly concave sides of each of the artificial petals of the first artificial petal element. With the glue on the artificial petals facing upwardly, the wire of the mold was inserted downwardly through the small hole in the artificial petal element until the coalescence at the base of the artificial petals touched the bottom of the mold head. The artificial petals were then wrapped around the mold head in the order (referenced to the first petal) first petal, adjacent petal, adjacent petal, opposite petal, and held until the glue along the equator and on lateral regions had dried at least sufficiently to hold the artificial petals in place. The lateral extremities of the first artificial petal when in place on the mold head did not quite overlap while the portions near the tip substantially sheathed the upper portion of the mold head. The portions near the tips of the other three artificial petals were progressively less enveloping of the upper portion of the mold head in accordance with the order in which they were positioned.

White glue was placed locally on only one lateral region of the slightly concave sides of each of the artificial petals of the second artificial petal element. With the glue on the artificial petals facing upwardly, the wire of the mold was inserted downwardly through the small hole in the second artificial petal element until the coalescence at the base of the artificial petals of the second artificial petal element touched the coalescence of the previously positioned first artificial petal element. The second petal element was rotated until the axes of symmetry through opposing sinuses was at about 45 degrees from the corresponding axes of symmetry of the first artificial petal element. Proceeding in clockwise order, the artificial petals of the second artificial petal element were then subsequently wrapped around the previously positioned artificial petals of the first artificial petal element and held until the glue on the lateral regions of the artificial petals of the second artificial petal element had dried at least sufficiently to hold the newly positioned artificial petals in place.

White glue was applied to the artificial petals of a third artificial petal element and the artificial petals were wrapped around the previously positioned artificial petals of the second artificial petal element, all in a manner analogous to that of the second artificial petal element, including the 45 degree rotational offset.

White glue was placed on the edge of a No. P-200B artificial calyx from the kit and the wire of the mold was inserted into the central hole of the artificial calyx. The artificial calyx was then pushed up the wire until it enveloped the coalescence of the previously positioned third petal element. The glue was allowed to dry.

A J740s artificial leaf from the kit comprises an artificial blade of sized green fabric which had been glued to a green paper-covered wire. The portion of the covered wire in contact with the artificial blade functions as an artificial midrib while the remainder functions as an artificial petiole. The artificial leaf was placed such that the artificial petiole portion of the covered wire was parallel to and in contact with the wire of the mold and such that the lower portion of the artificial blade was in contact with the lower portion of the artificial calyx. The lower portion of the artificial calyx, the artificial petiole portion of the covered wire, and the wire of the mold were wrapped together in helical fashion with green florist's tape, beginning at the lower portion of the artificial calyx and continuing past the lower end of the covered wire to the lower end of the wire of the mold, to form an artificial stem.

The tips of some of the artificial petals were bent back slightly into a recurved position. Upon minor adjustment of the artificial petals according to individual preference, the artificial rose was complete.

For a more complete description of artificial flowers having artificial petals of fragrance delivery devices of the present invention see application Ser. No. 250,015, filed Sept. 27, 1988, which is a continuation-in-part of application Ser. No. 110,147, filed Oct. 19, 1987, the entire disclosures of which are incorporated herein by reference.

EXAMPLE 40

A Nalgene filter holder with receiver (Catalog No. 300-4000) was modified by using the top which was threaded on the large end, the associated threaded bottom, and the intervening O-ring as a container for determining the rates of release of active agent from microporous materials. The procedure was to cut from microporous material a disc having a diameter as large as or a little larger than the interior of the container bottom. After treatment with active agent, the disc was placed on the interior of the container bottom. The O-ring was placed in position and the bottom and top were screwed together. Wax or high vacuum grease was placed on the outside of the joint to provide additional insurance against leakage. The assembled apparatus was analogous to a beaker with a disc of active agent-containing microporous material held flush against the bottom. The capacity of the assembled apparatus was about 300 milliliters. The apparatus was placed in a controlled substantially constant temperature water bath, an appropriate solvent was added, and the solvent was stirred with a glass stirrer. Samples were taken from time to time and analyzed for active agent. From this information release rates were calculated.

An 8 centimeter diameter disc cut from microporous material similar to that of Example 1 was extracted with 1,1,2-trichloro-1,2,2-trifluoroethane to remove substantially all of the residual processing plasticizer. The disc was placed in a desiccator for about 2 weeks to dry to a constant weight of 0.7813 gram. The disc was then soaked in a 50 percent by weight aqueous solution of procain hydrochloride. The disc was blotted with No. 41 Whatman filter paper and weighed. The weight was 1.9737 grams. The disc was dried overnight in the desiccator and weighed. The weight was 1.4386 grams. The container described above was assembled with a 1.0197 g portion of the disc in position and placed in a 33° C.-34° C. water bath. Two hundred milliliters of water buffered at pH 7.4 with $KH_2PO_4$ and $Na_2HPO_4$ was added to the container. Stirring was begun and the timer was started. Samples (3 milliliters each) were taken at timed intervals, diluted, and analyzed for procain hydrochloride using an ultraviolet spectrophotometer at 289.3 nanometers. The release rates, each averaged over the time interval since the previous sample showing an increase in concentration, were calculated. The results are shown in Table XV.

TABLE XV

| | Procain Hydrochloride Release Rates | | | |
|---|---|---|---|---|
| Cumulative Time, | Procain ® HCl Concentration, mg/L | | Extract Volume, | Release Rate |
| hours:minutes | Measured | Difference | milliliters | mg/min. |
| 0:01 | 750 | 750 | 200 | 150 |
| 0:02.5 | 1280 | 530 | 197 | 69.6 |
| 0:05 | 1290 | 10 | 194 | 0.8 |
| 0:07.5 | 1360 | 70 | 191 | 5.3 |
| 0:10 | 1400 | 40 | 188 | 3.0 |
| 0:12.5 | 1450 | 50 | 185 | 3.7 |
| 0:15 | 1390 | 0 | 182 | 0 |
| 0:20 | 1450 | 0 | 179 | 0 |
| 0:25 | 1415 | 0 | 176 | 0 |
| 0:30 | 1450 | 0 | 173 | 0 |
| 0:45 | 1460 | 10 | 170 | 0.1 |
| 1:00 | 1380 | 0 | 167 | 0 |
| 1:30 | 1500 | 40 | 164 | 0.1 |
| 2:00 | 1450 | 0 | 161 | 0 |
| 20:00 | 1670 | 170 | 158 | <0.1 |

EXAMPLE 41

An 8 centimeter diameter disc cut from microporous material similar to that of Example 1 was extracted with ethanol to remove substantially all of the residual processing plasticizer and then dried for about 2 days in a desiccator. The weight of the dried disc was 0.8502 gram. A solution of salicylic acid in ethanol was prepared by admixing 40 grams of salicylic acid and 113 milliliters of ethanol having a density of 0.789 gram/milliliter. The disc was soaked for one hour in the salicylic acid-ethanol solution. The disc was blotted with absorbent paper and weighed. The weight was 1.9502 grams. After drying overnight, the disc weighed 1.4780 grams. The container described in Example 40 was assembled with the disc in the position and placed in a 32° C. water bath. Two hundred milliliters of water buffered at pH 7.4 as in Example 40 was added to the container. Stirring was begun and the timer was started. Samples (3 milliliters each) were taken at timed intervals, diluted, and analyzed for salicylic acid by ultraviolet spectrophotometry and infrared spectroscopy. The release rates, each averaged over the time interval since the previous sample showing an increase in concentration, were calculated. The results are shown in Table XVI.

TABLE XVI

| | Salicylic Acid Release Rates | | | |
|---|---|---|---|---|
| Cumulative Time | Salicylic Acid Concentration, mg/L | | Extract Volume, | Release Rate |
| hours:minutes | Measured | Difference | milliliters | mg/min. |
| 0:01 | 257 | 257 | 200 | 51 |
| 0:02.5 | 502 | 245 | 197 | 32 |
| 0:05 | 711 | 209 | 194 | 16 |
| 0:07.5 | 854 | 143 | 191 | 11 |
| 0:10 | 931 | 77 | 188 | 5.8 |
| 0:12.5 | 1041 | 110 | 185 | 8.1 |
| 0:15 | 1134 | 93 | 182 | 6.8 |
| 0:20 | 1261 | 127 | 179 | 4.5 |
| 0:25 | 1340 | 79 | 176 | 2.8 |
| 0:30 | 1353 | 13 | 173 | 0.45 |
| 0:45 | 1375 | 22 | 170 | 0.25 |
| 1:00 | 1388 | 13 | 167 | 0.14 |
| 1:30 | 1405 | 17 | 164 | 0.09 |
| 2:00 | 1410 | 5 | 161 | 0.03 |
| 16:00 | 1511 | 101 | 158 | 0.02 |

EXAMPLE 42

An 8 centimeter diameter disc cut from microporous material similar to that of Example 1 was extracted with ethanol to remove substantially all of the residual processing plasticizer and then dried for about 2 days in a desiccator. The weight of the dried disc was 0.7854 gram. The disc was then exposed to vapors of hexamethyldisilazane for several hours. Upon completion of the hexamethyldisilazane vapor treatment the disc weighed 0.7874 gram. The disc was soaked for one hour in the salicylic acid ethanol solution of Example 41. The disc was blotted with absorbent paper and weighed. The weight was 1.7673 grams. The disc was then dried. The container described in Example 40 was assembled with the dried disc in position and placed in a 32° C. water bath. Two hundred milliliters of water buffered at pH 7.4 as in Example 40 was added to the container. Stirring was begun and the timer was started. Samples (3 milliliters each) were taken at timed intervals, diluted, and analyzed for salicylic acid by ultraviolet spectrophotometry, and infrared spectroscopy. The release rates, each averaged over the time interval since the previous sample showing an increase in concentration, were calculated. The results are shown in Table XVII.

TABLE XVII

| | Salicylic Acid Release Rates | | | |
|---|---|---|---|---|
| Cumulative Time, | Salicylic Acid Concentration, mg/L | | Extract Volume, | Release Rate |
| hours:minutes | Measured | Difference | milliliters | mg/min. |
| 0:01 | 224 | 224 | 200 | 45 |
| 0:02.5 | 442 | 218 | 197 | 29 |
| 0:05 | 607 | 165 | 194 | 13 |
| 0:07.5 | 740 | 133 | 191 | 10 |
| 0:10 | 839 | 99 | 188 | 7.4 |
| 0:12.5 | 936 | 97 | 185 | 7.2 |
| 0:15 | 1024 | 88 | 182 | 6.4 |
| 0:20 | 1138 | 114 | 179 | 4.1 |
| 0:25 | 1230 | 92 | 176 | 3.2 |
| 0:30 | 1257 | 27 | 173 | 0.93 |
| 0:45 | 1292 | 35 | 170 | 0.40 |
| 1:00 | 1318 | 26 | 167 | 0.29 |
| 1:30 | 1336 | 18 | 164 | 0.10 |
| 2:00 | 1362 | 26 | 161 | 0.14 |
| 20:00 | 1437 | 75 | 158 | 0.01 |

EXAMPLE 43

A 21.59 centimeter×27.94 centimeter sheet of the microporous material of Example 8 was treated on one side with a spray application of 0.50 gram of N-trimethoxysilylpropyl ethylene diamine triacetic acid, trisodium salt (Petrarch Systems T2913) in 10 milliliters of toluene. The sprayed sheet was heated in an air oven at 110° C. for 2 hours to couple the silane to the silica. The reverse side was then treated with 0.01 gram of hexamethyldisilazane (Petrarch Systems H7300) in 10 milliliters of dry methylene chloride by spray application. The sheet was allowed to dry in the hood for 2 hours at ambient temperature, then heated in an oven at 40° C. for 3 hours and finally at 110° C. for 30 minutes.

N-Trimethoxysilylpropyl ethylene diamine triacetic acid, sodium salt, is hydrophilic, whereas hexamethyldisilazane is hydrophobic. Consequently, the treated sheet had a hydrophilic surface and a hydrophobic opposite surface.

MVTR testing of both the treated microporous sheet and an untreated sheet of the microporous material of Example 8 was done using a modified ASTM E96 test procedure: Test Temperature was 21° C.; Relative Humidty was 60%; Air Velocity was 342 meters/minute. Each sample was tested twice, once with one surface facing the water of an upright cup, and then with the opposite surface facing the water of an upright cup. The results are shown in Table XVIII.

TABLE XVIII

Modified Moisture Vapor Transmission Rates

| Sample | Side Facing Water | Modified MVTR, $g/m^2$ day |
|---|---|---|
| Treated | Hydrophobic | 3427 |
| Treated | Hydrophilic | 1216 |
| Untreated | First | 3816 |
| Untreated | Opposite | 2823 |

The results show that the moisture vapor transmission rates for the treated sample were substantially different, depending upon whether the hydrophobic side or the hydrophilic side was facing the water. The results also show that the moisture vapor transmission rates for the untreated sample were significantly different, depending upon which side was facing the water.

EXAMPLE 44

A sample of microporous material similar to that of Example 8 (viz., unstretched microporous material, other portions of which were biaxially stretched to produce the product of Example 32), and samples of the biaxially stretched microporous materials of Examples 24, 31, 32, and 33, were tested for moisture vapor transmission rates according to the procedure of ASTM E96. For upright cup measurements, liquid water in the cup was not in contact with the microporous material. For inverted cup measurements, the cup was inverted so that liquid water in the cup contacted the microporous material. The results are shown in Table XIX.

TABLE XIX

Moisture Vapor Transmission Rates

| | MVTR, $g/m^2$ day | |
|---|---|---|
| Sample | Upright Cup | Inverted Cup |
| Similar to Example 8 | 947 | 17459 |
| Example 24 | 947 | 14043 |
| Example 31 | 982 | 14051 |
| Example 32 | 1004 | 15743 |
| Example 33 | 928 | 12073 |

EXAMPLE 45

A sample of microporous material similar to the microporous material of Example 1 and weighing 4.44 grams was extracted twice for 5 minutes with 50 milliliters of 1,1,2-trichloro-1,2,2-trifluoroethane and then air dried. The dried sample weighed 4.00 grams. A solution was prepared by admixing 2.5 grams of bis(hydrogenated tallow alkyl) dimethylammonium chloride (Arquad ® 2HT75; Akzo Chemie America) [CAS Registry No. 61789-80-8] and 100 milliliters of 2-propanol. The dried sample of microporous material was impregnated with the solution, dried under vaccuum, and then further dried in air. The treated sample weighed 5.64 grams and is useful for inclusion with clothes during drying to reduce accumulation of static electricity by the dried clothes.

Although the present invention has been described with reference to specific details of certain embodiments thereof, it is not intended that such details should be regarded as limitations upon the scope of the invention except insofar as they are included in the accompanying claims.

We claim:

1. An active agent delivery device which releases active agent over a prolonged period of time comprising:
    (a) microporous material comprising:
        (1) a matrix consisting essentially of essentially linear ultrahigh molecular weight polyolefin which is essentially linear ultrahigh molecular weight polyethylene having an intrinsic viscosity of at least about 18 deciliters/gram, essentially linear ultrahigh molecular weight polypropylene having an intrinsic viscosity of at least about 6 deciliters/gram, or a mixture thereof,
        (2) finely divided particulate substantially water-insoluble filler, of which at least about 50 percent by weight is siliceous, distributed throughout said matrix, said filler constituting from about 50 percent to about 90 percent by weight of said microporous material, and
        (3) a network of interconnecting pores communicating throughout said microporous material, said pores constituting more than 35 percent by volume of said microporous material.
    (b) a releasable active agent or precursor thereof associated with at least a portion of said filler.

2. The active agent delivery device of claim 1 wherein said essentially linear ultrahigh molecular weight polyolefin is essentially linear ultrahigh molecular weight polyethylene having an intrinsic viscosity of at least about 18 deciliters/gram.

3. The active agent delivery device of claim 2 wherein said ultrahigh molecular weight polyethylene has an intrinsic viscosity in the range of from about 18 to about 39 deciliters/gram.

4. The active agent delivery device of claim 2 wherein said filler constitutes from about 50 percent to about 85 percent by weight of said microporous material.

5. The active agent delivery device of claim 2 wherein said filler is silica.

6. The active agent delivery device of claim 2 wherein said filler is precipitated silica.

7. The active agent delivery device of claim 6 wherein said precipitated silica has an average ultimate particle size of less than about 0.1 micrometer.

8. The active agent delivery device of claim 2 wherein the volume average diameter of said pores as determined by mercury porosimetry is in the range of from about 0.02 to about 50 micrometers.

9. The active agent delivery device of claim 2 wherein said pores constitute from about 35 percent to about 95 percent by volume of said microporous material.

10. The active delivery device of claim 2 wherein said pores constitute from about 35 percent to about 80 percent by volume of said microporous material.

11. The active agent delivery device of claim 2 wherein said pores constitute from more than 80 percent to about 95 percent by volume of said microporous material.

12. The active agent delivery device of claim 2 wherein said active agent is medicament.

13. The active agent delivery device of claim 2 wherein said microporous material has been treated with one or more substances which alter the transmission characteristics of said microporous material.

14. The active agent delivery device of claim 1 wherein a reservoir of said releasable active agent or said precursor thereof is located on one side of said microporous material to replenish said microporous material with said releasable active agent or said precursor as said releasable active agent is released from said microporous material or as said precursor is consumed.

* * * * *

UNITED STATES PATENT AND TRADEMARK OFFICE
CERTIFICATE OF CORRECTION

PATENT NO. : 4,959,208

DATED : September 25, 1990

INVENTOR(S) : John M. Denison, et al.

It is certified that error appears in the above-identified patent and that said Letters Patent is hereby corrected as shown below:

In the title page of the patent, under Inventors, the following Inventors should be deleted:

Paritosh M. Chakrabarti, Malcolm Korach, Richard A. Schwarz and Robert B. Simmons.

The correct Inventors are as follows:

John M. Denison, Harlan B. Johnson, Dennis D. Leatherman, Linda P. Reinhardt, Melvin P. Wagner Signed and Sealed this Twelfth Day of May, 1992

Attest:

DOUGLAS B. COMER

*Attesting Officer*   *Acting Commissioner of Patents and Trademarks*